United States Patent [19]
Gaughan et al.

[11] 4,168,152
[45] Sep. 18, 1979

[54] HERBICIDAL COMPOSITIONS AND METHODS

[75] Inventors: Edmund J. Gaughan, Berkeley; Martin D. Mahoney, San Jose; Ferenc M. Pallos, Walnut Creek, all of Calif.

[73] Assignee: Stauffer Chemical Company, Westport, Conn.

[21] Appl. No.: 849,155

[22] Filed: Nov. 7, 1977

[51] Int. Cl.² ............................................. A01N 9/22
[52] U.S. Cl. .......................................... 71/93; 71/103
[58] Field of Search ............................................. 71/93

[56] References Cited
U.S. PATENT DOCUMENTS

| 3,799,760 | 3/1974 | Stephens | 71/103 |
| 3,923,494 | 12/1975 | Teach | 71/93 X |
| 3,933,894 | 1/1976 | Stephens | 71/103 X |
| 4,057,414 | 11/1977 | Fischer | 71/93 X |

FOREIGN PATENT DOCUMENTS 846894  4/1977  Belgium.

Primary Examiner—Joseph Paul Brust
Attorney, Agent, or Firm—Harry A. Pacini

[57] ABSTRACT

Crops are protected against injury from triazine herbicides by application of certain N-benzenesulfonyl carbamates as herbicide antidotes. The N-benzenesulfonyl carbamates have the general structural formula

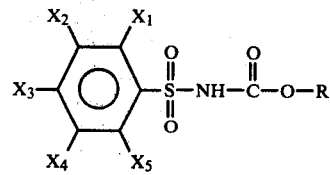

wherein each of $X_1$, $X_2$, $X_3$, $X_4$, and $X_5$ is independently selected from the group consisting of hydrogen, halogen and lower alkyl, with the proviso that when $X_3$ is lower alkyl, $X_1$ and $X_5$ are not both hydrogen; and R is selected from the group consisting of lower alkyl, alkenyl, alkynyl and alkyl and alkenyl radicals substituted with up to five halo atoms.

44 Claims, No Drawings

HERBICIDAL COMPOSITIONS AND METHODS

BACKGROUND OF THE INVENTION

This invention relates to the use of certain N-benzenesulfonyl carbamates as antidotes to protect crops from herbicidal injury due to use of triazine herbicides.

DESCRIPTION OF THE PRIOR ART

Certain N-benzenesulfonyl carbamates are disclosed in U.S. Pat. No. 3,799,760, J. A. Stevens, Mar. 26, 1974 and U.S. Pat. No. 3,933,894, J. A. Stevens, Jan. 20, 1976 to be useful as herbicides. Belgian Pat. No. 846,894, Stauffer Chemical Company, Apr. 1, 1977, reports the use of N-benzenesulfonyl carbamates as herbicidal antidotes to protect crops from injury by thiocarbamate type herbicides.

DESCRIPTION OF THE INVENTION

It has now been discovered that N-benzenesulfonyl carbamates of the general structural formula

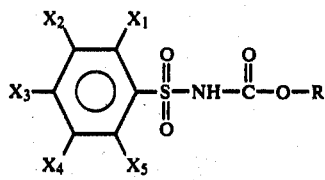

wherein each of $X_1$, $X_2$, $X_3$, $X_4$ and $X_5$ is independently selected from the group consisting of hydrogen, halogen and lower alkyl, with the proviso that when $X_3$ is lower alkyl, $X_1$ and $X_5$ are not both hydrogen; and R is selected from the group consisting of lower alkyl, alkenyl, alkynyl and alkyl and alkenyl radicals substituted with up to five halo atoms are effective antidotes for protecting crops from injury due to triazine herbicides.

In the above definitions, the term lower alkyl refers to straight and branched chain alkyl radicals having 1 to 4 carbon atoms, i.e., methyl, ethyl, propyl, isopropyl, butyl, isobutyl, sec-butyl and tert-butyl. The term alkenyl refers to straight and branched chain alkenyl radicals containing 3 to 6 carbon atoms, for example propen-1-yl, 3-methylpropen-1-yl, buten-1-yl, penten-1-yl, hexen-1-yl, and position isomers thereof. The term alkynyl refers to straight and branched chain alkynyl radicals containing 3 to 6 carbon atoms, for example, propyn-1-yl, 1-methylpropyn-2-yl, 1-methylbutyn-2-yl, butyn-1-yl, pentyn-1-yl, hexyn-1-yl, and positions isomers thereof. The term haloalkyl and the term haloalkenyl refer to alkyl and alkenyl radicals as defined above substituted with up to five, and preferably up to three, halo atoms. Halo includes chlorine, bromine, fluorine and iodine, with chlorine and fluorine being preferred.

Particularly preferred are compounds in which each of $X_1$, $X_2$, $X_4$ and $X_5$ are hydrogen, $X_3$ is hydrogen, chlorine or bromine and R is as defined above. Another preferred subgenus includes compounds in which $X_1$, $X_3$, and $X_5$ are lower alkyl, particularly methyl, and R is as defined above. Still another preferred subgenus includes those compounds in which $X_1$, $X_2$, $X_4$ and $X_5$ are hydrogen, $X_3$ is hydrogen, chlorine or bromine and R is methyl, ethyl, isopropyl, 2,2-dichloroethyl, 2,2,2-trichloroethyl, 2,2,2-trifluoroethyl, allyl, 2-chloroallyl, propargyl or 2-butyn-1-yl.

Illustrative examples of suitable N-benzenesulfonyl carbamates are: N-(4-chlorobenzenesulfonyl)-propargyl carbamate, N-(4-chlorobenzenesulfonyl)-ethyl carbamate, N-(4-chlorobenzenesulfonyl)-2,2-dichloroethyl carbamate, N-(4-chlorobenzenesulfonyl)-2,2,2-trifluoroethyl carbamate, N-(4-chlorobenzenesulfonyl)-2-chloroallyl carbamate, N-(4-chlorobenzenesulfonyl)-2-butyn-1-yl carbamate, N-(benzenesulfonyl)-propargyl carbamate, N-(4-bromobenzenesulfonyl)-propargyl carbamate, N-(4-chlorobenzenesulfonyl)-allyl carbamate, N-(benzenesulfonyl)-2,2,2-trifluoroethyl carbamate, N-(4-chlorobenzenesulfonyl)-methyl carbamate, N-(2,4,6-trimethylbenzenesulfonyl)-propargyl carbamate, N-(benzenesulfonyl)-isopropyl carbamate, N-(3-chlorobenzenesulfonyl)-2,2,2-trifluoroethyl carbamate, N-(benzenesulfonyl)-2,2,2-trichloroethyl carbamate, N-(3,5-dichlorobenzenesulfonyl)-propargyl carbamate, N-(3-methylbenzenesulfonyl)-2,2-dichloroethyl carbamate, N-(2,4,6-triethylbenzenesulfonyl)-allyl carbamate, N-(2-isopropylbenzenesulfonyl)-2-chloroallyl carbamate, N-(4-iodobenzenesulfonyl)-propyl carbamate, N-(4-iodobenzenesulfonyl)-propargyl carbamate, N-(3,5-dimethylbenzenesulfonyl)-2,2,2-trifluoroethyl carbamate, N-(2,6-diethylbenzenesulfonyl)-propargyl carbamate and N-(2,4,6-trichlorobenzenesulfonyl)-2-butyn-1-yl carbamate.

The N-benzenesulfonyl carbamates utilized in accordance with the instant invention can be prepared by known methods. One general method of preparing N-benzenesulfonyl alkynyl carbamates is the reaction of an appropriate alkynol with benzenesulfonyl isocyanate. More particularly, the reaction is performed in the presence of a solvent such as benzene or chloroform with catalytic amounts of triethylamine and dibutyl tin dilaurate. In some instances, a catalyst is not required. After the reaction is complete, the product is recovered by filtration or evaporation of the solvent. If necessary, the product can be recrystallized from a suitable solvent.

A general method of preparing N-benzenesulfonyl alkyl carbamates is the reaction of an appropriate benzenesulfonamide with an alkyl chloroformate in the presence of potassium carbonate. A solvent is normally employed to facilitate the reaction and aid in the work-up of the product. After filtration, extraction and drying, the product can be purified further by tritutation with hexane or recrystallization from a suitable solvent.

The following examples illustrate the preparation of N-benzenesulfonyl carbamates.

EXAMPLE 1

Preparation of N-(p-chlorobenzenesulfonyl)-propargyl carbamate

To a solution of 1.7 grams (0.03 mole) of propargyl alcohol in 20 milliliters of benzene containing one drop of triethylamine and one drop of dibutyl tin dilaurate was added a solution of 6.5 grams (0.03 mole) of p-chlorobenzenesulfonyl isocyanate in 25 milliliters of benzene. The reaction was exothermic and the temperature was allowed to rise to 30° C. The mixture was stirred several hours at room temperature and the precipitated solid was filtered and washed with a small amount of hexane and dried. There was obtained a yield of 8.0 grams (98% of theory) of the title compound, m.p. 106°–108° C. A pure sample melted at 120.5°–121° C. The structure was confirmed by infrared, nuclear magnetic resonance, and mass spectroscopy.

EXAMPLE 2

Preparation of N-(p-chlorobenzenesulfonyl)-ethyl carbamate p-Chlorobenzenesulfonamide (6.1 grams, 0.032 mole), potassium carbonate (10.8 grams, 0.078 mole), and ethyl chloroformate (3.7 grams, 0.034 mole) in 40 milliliters of acetone were stirred and refluxed for two hours. During the heating period the mixture became thick and was diluted with another 30 milliliters of acetone. The cooled mixture was poured into 150 milliliters of water and filtered through Celite. The filtrate was acidified with hydrochloric acid with cooling (pH about 2) and the product extracted with benzene. The extract was washed with water and dried over anhydrous magnesium sulfate. Removal of the solvent left the title compound as a solid. There was obtained a yield of 5.5 grams (65% of theory) of the title compound, m.p. 85°–90° C. The structure was confirmed by IR.

Other N-benzenesulfonyl carbamates typical of those useful as antidotes to protect crops from triazine herbicides, are listed in the following Table I. Compound numbers have been assigned to each compound and are then used throughout the remainder of the specification.

TABLE I $$X_3-\underset{X_4\ X_5}{\underset{|}{\overset{X_2\ X_1}{\overset{|}{\bigcirc}}}}-\overset{O}{\underset{O}{\overset{\|}{S}}}-NH-\overset{O}{\overset{\|}{C}}-O-R$$

| Compound No. | $X_1$ | $X_2$ | $X_3$ | $X_4$ | $X_5$ | R |
|---|---|---|---|---|---|---|
| 1 | H | H | Cl | H | H | $-CH_2C\equiv CH$ |
| 2 | H | H | Cl | H | H | $-C_2H_5$ |
| 3 | H | H | Cl | H | H | $-CH_2CHCl_2$ |
| 4 | H | H | Cl | H | H | $-CH_2CF_3$ |
| 5 | H | H | Cl | H | H | $-\underset{CH_2C=CH_2}{\overset{Cl}{\underset{|}{}}}$ |
| 6 | H | H | Cl | H | H | $-CH_2C\equiv C-CH_3$ |
| 7 | H | H | H | H | H | $-CH_2C\equiv CH$ |
| 8 | H | H | Br | H | H | $-CH_2C\equiv CH$ |
| 9 | H | H | Cl | H | H | $-CH_2CH=CH_2$ |
| 10 | H | H | H | H | H | $-CH_2CF_3$ |
| 11 | H | H | Cl | H | H | $-CH_3$ |
| 12 | $CH_3$ | H | $CH_3$ | H | $CH_3$ | $-CH_2C\equiv CH$ |
| 13 | H | H | H | H | H | $-i-C_3H_7$ |
| 14 | H | Cl | H | H | H | $-CH_2CF_3$ |
| 15 | H | H | H | H | H | $-CH_2CCl_3$ |

The use of these compounds as an antidote to protect cotton and soybeans from injury by triazine herbicides such as 2-chloro-4-ethylamine-6-isopropylamino-S-triazine, (commonly known as atrazine) is demonstrated by the following evaluation procedures.

EXAMPLE 3

This example demonstrates the protection of cotton from injury due to atrazine. As a preparatory step, the following stock solutions were prepared:

Antidote Stock Solutions

Thirty-nine milligrams of each antidote compound to be tested was dissolved in 10 milliliters (ml) of acetone to provide a solution such that 5 ml of solution is equivalent to a rate of 5.0 pounds per acre (lb/A); 2.5 ml is equivalent to 2.5 lb/A, and 2.0 ml is equivalent to 2.0 lb/A when applied to a 6"×9" flat.

Thirty-one milligrams of each antidote test compound was dissolved in 40 ml acetone to provide a solution such that 5.0 ml is equivalent to a rate of 1.0 lb/A and 2.5 ml is equivalent to 0.5 lb/A when applied to a 6"×9" flat.

Herbicide Stock Solution

One hundred and forty-six milligrams of AAtrex® 80W (atrazine) was dissolved in 75 milliliters of water to provide a solution such that 5.0 ml is equivalent to 2.0 lb/A and 2.5 ml is equivalent to 1.0 lb/A when applied to a 6"×9" flat.

Pre-Plant Incorporation (Tank Mix) Evaluation

Small flats were filled with Felton loamy sand soil. The soil from each flat was transferred to a five gallon cement mixer. A tank mix was prepared by mixing the appropriate quantities of herbicide and antidote stock solutions to provide the application rates specified in Table II. The tank mix was then added to the soil while in the cement mixer to simultaneously incorporate both herbicide and antidote into the soil. The soil was transferred back into the flats. Control flats of soil containing only herbicide were similarly prepared for use in comparison ratings.

One pint of soil was removed from each flat and reserved for later use in covering the seeds. Rows ¼ inch deep were made lengthwise in the flats, cotton seeds were placed in the rows and covered with the reserved soil. The flats were placed in a greenhouse and maintained at a temperature of 70°–90° F. Flats were watered by sprinkling as needed. Injury ratings of the antidote treated and control flats were taken after four weeks. Results are shown in Table II as percent injury to cotton in the antidote treated flat/the percent injury to cotton in the control flats.

In addition to cottons seeds (*Gossypium hirsutum*), mustard (*Brassica juncea*) and curly dock (*Rumex crispus*) seeds were planted in the treated and control flats. There was no protection of these weeds by the antidote test compound in the treated flats.

TABLE II

| Antidote Compound | Atrazine Rate | Protection of Cotton Results at Indicated Antidote Rates | | | | |
|---|---|---|---|---|---|---|
| | | 0.5 lb/A | 1.0 lb/A | 2.0 lb/A | 2.5 lb/A | 5.0 lb/A |
| 1 | 1 lb/A | — | 50/100 | — | 30/100 | 20/100 |
| 1 | 1 lb/A | 70/70 | 100/70 | 20/70 | — | — |
| 1 | 1 lb/A | | 100/100 | | | 20/100 |
| 1 | 2 lb/A | 40/100 | 100/100 | 50/100 | — | — |
| 2 | 1 lb/A | 30/70 | 40/70 | 0/70 | — | — |
| 2 | 1 lb/A | — | 10/100 | 30/100 | 20/100 | |
| 2 | 1 lb/A | — | 100/100 | — | — | 50/100 |
| 2 | 2 lb/A | 90/100 | 60/100 | 60/100 — | — | |
| 3 | 1 lb/A | — | 40/100 | — | — | 40/100 |
| 4 | 1 lb/A | — | 30/100 | — | — | 30/100 |
| 5 | 1 lb/A | — | 90/100 | — | — | 50/100 |

TABLE II-continued

| Antidote Compound | Atrazine Rate | Protection of Cotton Results at Indicated Antidote Rates | | | | |
|---|---|---|---|---|---|---|
| | | 0.5 lb/A | 1.0 lb/A | 2.0 lb/A | 2.5 lb/A | 5.0 lb/A |
| 6 | 1 lb/A | — | 100/100 | — | — | 30/100 |
| 7 | 1 lb/A | — | 100/100 | — | — | 30/100 |
| 8 | 1 lb/A | — | 100/100 | — | — | 10/100 |
| 9 | 1 lb/A | — | 100/100 | — | — | 20/100 |
| 10 | 1 lb/A | — | 100/100 | — | — | 80/100 |
| 11 | 1 lb/A | — | 70/100 | — | — | 20/100 |
| 12 | 1 lb/A | — | 80/100 | — | — | 0/100 |
| 13 | 1 lb/A | — | 40/100 | — | — | 60/100 |

EXAMPLE 4

This example demonstrates the protection of soybeans from injury due to triazine herbicides.

As a preparatory step in the following stock solutions were prepared:
Antidote Stock Solutions Sixty-eight milligrams of each antidote compound to be tested was dissolved in 50 ml acetone to provide a solution such that 1.0 ml of solution is equivalent to a rate of 0.5 lb/A, 2.0 ml is equivalent to 1.0 lb/A and 4.0 ml is equivalent to 2.0 lb/A when applied to a 5"×7" flat.
Herbicide Stock Solutions 2-chloro-4-ethylamino-6-isopropylamino-s-triazine (AAtrex ® 80W)

Fifty-one milligrams of AAtrex 80W was dissolved in 150 ml water to provide a solution such that 1.0 ml of solution is equivalent to a rate of 0.1 lb/A, 2.5 ml is equivalent to 0.25 lb/A and 5.0 ml is equivalent to 0.5 lb/A when applied to a 5"×7" flat.

2-(4-chloro-6-ethylamino-s-triazin-2-ylamino)-2-methylpropionitrile (BLADEX ® 80W)

Forty-two milligrams of BLADEX 80W was dissolved in 125 ml of water to provide a solution such that 5 ml of solution is equivalent to a rate of 0.5 lb/A when applied to a 5"×7" flat.

4-amino-6-tert.butyl-3-(methylthio)-1,2,4-triazin-5-(4H)-one (SENCOR ® 75W)

Forty-five milligrams of SENCOR 75W was dissolved in 125 ml water to provide a solution such that 5.0 ml of solution is equivalent to a rate of 0.5 lb/A when applied to a 5"×7" flat.

The preplant incorporation (tank mix) evaluation procedure described in Example 3 was repeated using the herbicide and stock solutions prepared above and using as the crop seed, soybeans (*Glycine max*), and as the weeds, watergrass (*Echinchloa crusgalli*), mustard (*Brassica juncea*), and curly dock (*Rumex crispus*). Slight protection of the weeds by antidote compounds 10 and 15 was noted when atrazine was used as the herbicide and no protection was observed by any of the other antidote compounds. No protection of weeds was observed when BLADEX or SENCOR was used. Results are shown in Table 3 as percent injury to soybeans in the antidote treated flat/percent injury to soybeans in the control flat.

TABLE III

| Antidote Compound | Herbicide | Protection of Soybeans Herbicide Rate (lb/A) | Results at Indicated Antidote Rates | | |
|---|---|---|---|---|---|
| | | | 0.5 lb/A | 1.0 lb/A | 2.0 lb/A |
| 1 | ATRAZINE | 0.1 | 10/100 | 0/100 | 0/0 |
| 1 | | 0.25 | 50/100 | 60/100 | 90/100 |
| 1 | | | 100/100 | 100/100 | 90/100 |
| 1 | | | — | — | 100/100 |
| 1 | | 0.5 | 100/100 | 100/100 | 100/100 |
| 2 | | 0.1 | 10/100 | 10/100 | 0/0 |
| 2 | | | — | 20/100 | 10/10 |
| 2 | | | — | — | 0/100 |
| 2 | | 0.25 | 5/100 | 100/100 | 0/100 |
| 2 | | | 20/100 | 10/100 | 100/100 |
| 2 | | | 100/100 | | 10/100 |
| 2 | | | — | — | 100/100 |
| 2 | | 0.5 | 0/100 | 100/100 | 90/100 |
| 2 | | | — | 100/100 | 100/100 |
| 2 | | | — | — | 100/100 |
| 10 | | 0.25 | 20/100 | 50/100 | 20/100 |
| 11 | | 0.25 | 100/100 | 100/100 | 30/100 |
| 15 | | 0.25 | 20/100 | 40/100 | 0/100 |
| 16 | | 0.25 | 100/100 | 100/100 | 100/100 |
| 10 | BLADEX | 0.5 | 70/100 | 60/100 | 100/100 |
| 11 | | 0.5 | 100/100 | 100/100 | 50/100 |
| 15 | | 0.5 | 100/100 | 70/100 | 50/100 |
| 16 | | 0.5 | 20/100 | 100/100 | 70/100 |
| 1 | SENCOR | 0.5 | 50/85 | 85/85 | 85/85 |
| 2 | | 0.5 | 85/85 | 85/85 | 85/85 |
| 10 | | 0.5 | 85/85 | 85/85 | 85/85 |
| 11 | | 0.5 | 70/85 | 85/85 | 85/85 |
| 15 | | 0.5 | 85/85 | 85/85 | 85/85 |
| 16 | | 0.5 | 85/85 | 85/85 | 85/85 |

The above examples illustrate the use of certain N-benzenesulfonyl carbamates as herbicide antidotes to protect crops from injury by triazine herbicide by incorporating the antidote and herbicide as a tank mixture into the soil. The use of other triazine herbicides and other methods of application can be used, if desired. Illustrative examples of triazine herbicides include, for example, 2-chloro-4-ethylamino-6-isopropylamino-s-triazine, 2-(4-chloro-6-ethylamino-s-triazin-2-yl-amino)-2-methylpropionitrile, 2,4-bis(isopropylamino)-6-methylthio-s-triazine, 2-[(4-chloro-6-cyclopropylamino-1,3,5-triazin-2-yl)-amino]-2-methylpropionitrile, 2-ethylamino-4-isopropylamino-6-methylthio-s-triazine, 2-chloro-4,6-bis(isopropylamino)-s-triazine, 2-chloro-4,6-bis(ethylamino)-s-triazine and 4-amino-6-tert.butyl-3-methylthio-1,2,4-triazin-5(4H)-one.

In general, antidotes are used in a formulation containing the antidote and an inert carrier. The herbicide can be included in the same formulation if desired. Such formulations can take the form of dusts, wettable powders, granules, solutions of emulsifiable concentrates. Numerous methods of antidote application are well known, for example, the antidote can be incorporated into the soil before, after or simultaneously with the herbicde. Solutions of antidote and herbicide can also be combined to form a tank mix which can be applied onto the surface of the soil or incorporated into the soil. In another method, the antidote can be directly applied into the seed furrow before or after crop seed placement, prior to covering the seeds with soil. This in-furrow method economically and effectively places the antidote immediately adjacent the crop seed to be protected from herbicidal injury. The in-furrow application can take place before or after herbicide has been applied to the soil. It is also possible to treat the crop seeds with the antidote prior to planting.

As used in this specification, the term herbicide refers to a compound that selectively controls, prevents, or inhibits the growth of vegetation or plants. Herbicides are generally applied to the soil wherein control of undesired vegetation is sought. In agricultural use, the herbicide can be applied to the soil before, after or simultaneously with planting of the crop seeds. The amount of herbicide employed in a given situation will depend on the particular herbicide used, the crop to be grown in the field, the types of weeds to be controlled and the degree of control desired. Herbicides are usually employed at a rate of about 0.05 to about 50 pounds per acre with a rate of about 1.0 to about 20 pounds per acre being preferred.

The term herbicide antidote refers to a compound which, when applied to the crop seed or the soil in which the crop seed is or will be planted, counteracts the growth controlling injurious effect of the herbicide on the crop. The term antidotally effective amount refers to the amount of the antidote which when applied to the crop seed or soil achieves the desired protection of the crop. This amount will vary widely, depending on the particular herbicide used and the method of application of the antidote. One skilled in the art, with the teaching of this specification before him, will be able, without undue experimentation, to determine the antidotally effective amount of the N-benzenesulfonyl carbamate to protect crops from injury by triazine herbicides. The amount of antidote employed can range from about 0.05 to about 50 pounds per acre. A rate of application of about 1 to about 10 pounds per acre is preferred.

In general, the amount of antidote compound used in proportion to the amount of herbicide used will be from about 0.001 to about 50, preferably about 0.01 to about 20 parts by weight of antidote per part herbicide.

What is claimed is:

1. A herbicidal composition consisting essentially of a herbicidally effective amount of a triazine herbicide and a non-phytotoxic antidotally effective amount to protect crops from injury by said triazine herbicide of a N-benzenesulfonyl carbamate of the formula

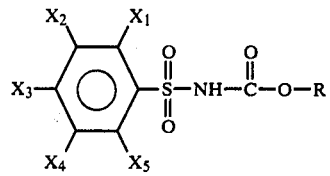

wherein $X_1$, $X_2$, $X_3$, $X_4$ and $X_5$ is independently selected from the group consisting of hydrogen, halogen, and lower alkyl containing 1 to 4 carbon atoms, with the proviso that when $X_3$ is lower alkyl, $X_1$ and $X_5$ are not both hydrogen; and R is selected from the group consisting of lower alkyl containing 1 to 4 carbon atoms, alkenyl containing 3 to 6 carbon atoms, alkynyl containing 3 to 6 carbon atoms and alkyl and alkenyl radicals containing 1 to 4 and 3 to 6 carbon atoms, respectively, substituted with up to five halo atoms, and wherein said N-benzenesulfonyl carbamate is antidotally active with said triazine herbicide.

2. A composition of claim 1 wherein said triazine herbicide is 2-chloro-4-ethylamino-6-isopropylamino-s-triazine.

3. A composition of claim 1 wherein said triazine herbicide is 2-(4-chloro-6-ethylamino-s-triazin-2-ylamino)-2-methylpropionitrile.

4. A composition of claim 1 wherein said triazine herbicide is 4-amino-6-tert.butyl-3-(methylthio)-1,2,4-triazin-5(4H)-one.

5. A composition of claim 1 wherein each of $X_1$, $X_2$, $X_4$ and $X_5$ are hydrogen and $X_3$ is hydrogen, chlorine or bromine.

6. A composition of claim 1 wherein each of $X_1$, $X_3$, and $X_5$ are lower alkyl and each of $X_2$ and $X_4$ are hydrogen.

7. A composition of claim 1 wherein each of $X_1$, $X_2$, $X_4$ and $X_5$ are hydrogen, $X_3$ is hydrogen, chlorine or bromine and R is selected from the group consisting of methyl, ethyl, isopropyl, 2,2-dichloroethyl, 2,2,2-trichloroethyl, 2,2,2-trifluoroethyl, allyl, 2-chloroallyl, propargyl and 2-butyn-1-yl.

8. The composition of claim 1 wherein said benzenesulfonyl carbamate is N-(4-chlorobenzenesulfonyl)-propargyl carbamate.

9. The composition of claim 1 wherein said benzenesufonyl carbamate is N-(4-chlorobenzenesulfonyl)-ethyl carbamate.

10. The composition of claim 1 wherein said benzenesulfonyl carbamate is N-(4-chlorobenzenesulfonyl)-2,2-dichloroethyl carbamate.

11. The composition of claim 1 wherein said benzenesulfonyl carbamate is N-(4-chlorobenzenesulfonyl)-2,2,2-trifluoroethyl carbamate.

12. The composition of claim 1 wherein said benzenesulfonyl carbamate is N-(4-chlorobenzenesulfonyl)-2-chloroallyl carbamate.

13. The composition of claim 1 wherein said benzenesulfonyl carbamate is N-(4-chlorobenzenesulfonyl)-2-butyn-1-yl carbamate.

14. The composition of claim 1 wherein said benzenesulfonyl carbamate is N-(benzenesulfonyl)-propargyl carbamate.

15. The composition of claim 1 wherein said benzenesulfonyl carbamate is N-(4-bromobenzenesulfonyl)-propargyl carbamate.

16. The composition of claim 1 wherein said benzenesulfonyl carbamate is N-(4-chlorobenzenesulfonyl)-allyl carbamate.

17. The composition of claim 1 wherein said benzenesulfonyl carbamate is N-(benzenesulfonyl)-2,2,2-trifluoroethyl carbamate.

18. The composition of claim 1 wherein said benzenesulfonyl carbamate is N-(4-chlorobenzenesulfonyl)-methyl carbamate.

19. The composition of claim 1 wherein said benzenesulfonyl carbamate is N-(2,4,6-trimethylbenzenesulfonyl)-propargyl carbamate.

20. The composition of claim 1 wherein said benzenesulfonyl carbamate is N-(benzenesulfonyl)-isopropyl carbamate.

21. The composition of claim 1 wherein said benzenesulfonyl carbamate is N-(3-chlorobenzenesulfonyl)-2,2,2-trifluoroethyl carbamate.

22. The composition of claim 1 wherein said benzenesulfonyl carbamate is N-(benzenesulfonyl)-2,2,2-trichloroethyl carbamate.

23. A method of protecting crops from injury from a triazine herbicide consisting essentially of applying to the soil a herbicidally effective amount of a triazine herbicide and a non-phytotoxic antidotally effective amount to protect crops from injury by said triazine herbicide of a N-benzenesulfonyl carbamate of the formula

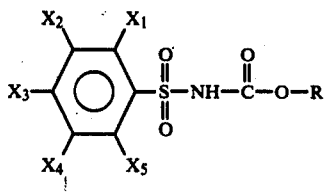

wherein each of $X_1$, $X_2$, $X_3$, $X_4$ and $X_5$ is independently selected from the group consisting of hydrogen, halogen, and lower alkyl containing 1 to 4 carbon atoms, with the proviso that when $X_3$ is lower alkyl, $X_1$ and $X_5$ are not both hydrogen; and R is selected from the group consisting of lower alkyl containing 1 to 4 carbon atoms, alkenyl containing 3 to 6 carbon atoms, alkynyl containing 3 to 6 carbon atoms and alkyl and alkenyl radicals containing 1 to 4 and 3 to 6 carbon atoms, respectively, substituted with up to five halo atoms, and wherein said N-benzenesulfonyl carbamate is antidotally active with said triazine herbicide.

24. A method of claim 23 wherein said triazine herbicide is 2-chloro-4-ethylamino-6-isopropylamino-s-triazine.

25. A method of claim 23 wherein said triazine herbicide is 2-(4-chloro-6-ethylamino-s-triazin-2-ylamino)-2-methylpropionitrile.

26. A method of claim 23 wherein said triazine herbicide is 4-amino-6-tert.butyl-3-(methylthio)-1,2,4-triazin-5(4H)-one.

27. A method of clam 23 wherein each of $X_1$, $X_2$, $X_4$ and $X_5$ are hydrogen and $X_3$ is hydrogen, chlorine or bromine.

28. A method of claim 23 wherein each of $X_1$, $X_3$ and $X_5$ are lower alkyl and each of $X_2$ and $X_4$ are hydrogen.

29. The method of claim 23 wherein each of $X_1$, $X_2$, $X_4$ and $X_5$ are hydrogen, $X_3$ is hydrogen, chlorine or bromine, and R is selected from the group consisting of methyl, ethyl, isopropyl, 2,2-dichloroethyl, 2,2,2-trichloroethyl, 2,2,2-trifluoroethyl, allyl, 2-chloroallyl, propargyl and 2-butyn-1-yl.

30. The method of claim 23 wherein said benzenesulfonyl carbamate is N-(4-chlorobenzenesulfonyl)-propargyl carbamate.

31. The method of claim 23 wherein said benzenesulfonyl carbamate is N-(4-chlorobenzenesulfonyl)-ethyl carbamate.

32. The method of claim 23 wherein said benzenesulfonyl carbamate is N-(4-chlorobenzenesulfonyl)-2,2-dichloroethyl carbamate.

33. The method of claim 23 wherein said benzenesulfonyl carbamate is N-(4-chlorobenzenesulfonyl)-2,2,2-trifluoroethyl carbamate.

34. The method of claim 23 wherein said benzenesulfonyl carbamate is N-(4-chlorobenzenesulfonyl)-2-chloroallyl carbamate.

35. The method of claim 23 wherein said benzenesulfonyl carbamate is N-(4-chlorobenzenesulfonyl)-2-butyn-1-yl carbamate.

36. The method of claim 23 wherein said benzenesulfonyl carbamate is N-(benzenesulfonyl)-propargyl carbamate.

37. The method of claim 23 wherein said benzenesulfonyl carbamate is N-(4-bromobenzenesulfonyl)-propargyl carbamate.

38. The method of claim 23 wherein said benzenesulfonyl carbamate is N-(4-chlorobenzenesulfonyl)-allyl carbamate.

39. The method of claim 23 wherein said benzenesulfonyl carbamate is N-(benzenesulfonyl)-2,2,2-trifluoroethyl carbamate.

40. The method of claim 23 wherein said benzenesulfonyl carbamate is N-(4-chlorobenzenesulfonyl)-methyl carbamate.

41. The method of claim 23 wherein said benzenesulfonyl carbamate is N-(2,4,6-trimethylbenzenesulfonyl)-propargyl carbamate.

42. The method of claim 23 wherein said benzenesulfonyl carbamate is N-(benzenesulfonyl)-isopropyl carbamate.

43. The method of claim 23 wherein said benzenesulfonyl carbamate is N-(3-chlorobenzenesulfonyl)-2,2,2-trifluoroethyl carbamate.

44. The method of claim 23 wherein said benzenesulfonyl carbamate is N-(benzenesulfonyl)-2,2,2-trichloroethyl carbamate.

* * * * *